United States Patent
Lindstrom

(10) Patent No.: US 8,858,627 B1
(45) Date of Patent: Oct. 14, 2014

(54) ACCOMODATIVE INTRAOCULAR LENS

(76) Inventor: Richard L. Lindstrom, Wayzata, MN (US)

( * ) Notice: Subject to any disclaimer, the term of this patent is extended or adjusted under 35 U.S.C. 154(b) by 835 days.

(21) Appl. No.: 12/584,689

(22) Filed: Sep. 10, 2009

Related U.S. Application Data

(60) Provisional application No. 61/273,727, filed on Aug. 7, 2009, provisional application No. 61/275,092, filed on Aug. 25, 2009.

(51) Int. Cl.
*A61F 2/16* (2006.01)

(52) U.S. Cl.
USPC .......... 623/6.37; 623/6.28; 623/6.4; 623/6.23

(58) Field of Classification Search
USPC ................................. 623/6.13, 6.26
See application file for complete search history.

(56) References Cited

U.S. PATENT DOCUMENTS

| | | | |
|---|---|---|---|
| 2005/0107873 A1* | 5/2005 | Zhou | 623/6.13 |
| 2007/0021831 A1* | 1/2007 | Clarke | 623/6.13 |
| 2007/0078515 A1* | 4/2007 | Brady | 623/6.37 |

* cited by examiner

*Primary Examiner* — David H Willse
*Assistant Examiner* — Tiffany Shipmon
(74) *Attorney, Agent, or Firm* — Law Offices of Steven W. Weinrieb

(57) ABSTRACT

An accommodative intraocular lens having a soft deformable resilient inner lens portion or core with an exposed anterior inner optic surface and exposed posterior optic surface, the surfaces responsively becoming simultaneously optically steeper and moving axially away from each other. The exposed anterior and posterior surfaces of the inner lens portions may be spherically shaped or aspherically shaped and the shape of the outer lens portion may be spherically or aspherically shaped.

15 Claims, 19 Drawing Sheets

ISOMETRIC VIEW – SPHERIC OUTER, SPHERIC INNER

EXPLODED ISOMETRIC VIEW – SPHERIC OUTER, SPHERIC INNER

ANTERIOR VIEW – SPHERIC OUTER, SPHERIC INNER

POSTERIOR VIEW – SPHERIC OUTER, SPHERIC INNER

CROSS SECTION (relaxed) – SPHERIC OUTER, SPHERIC INNER

CROSS SECTION (compressed) – SPHERIC OUTER, SPHERIC INNER

SIDE VIEW – SPHERIC OUTER, SPHERIC INNER

SIDE VIEW – SPHERIC OUTER, SPHERIC INNER

SIDE VIEW (relaxed) – SPHERIC OUTER, SPHERIC INNER

SIDE VIEW (compressed) – SPHERIC OUTER, SPHERIC INNER

SIDE VIEW-SPHERIC OUTER, ASPHERIC INNER

SIDE VIEW-ASPHERIC OUTER, SPHERIC INNER

SIDE VIEW-ASPHERIC OUTER, ASPHERIC INNER

ACCOMODATIVE INTRAOCULAR LENS

CROSS REFERENCES TO RELATED APPLICATIONS

This patent application claims benefit from the earlier filed U.S. Provisional Application No. 61/273,727 filed Aug. 7, 2009, entitled "Blended Trispheric and Blended Triaspheric Accommodative Intraocular Lens", and is hereby incorporated into this application by reference as if fully set forth herein.

This patent application also claims benefit from the earlier filed U.S. Provisional Application No. 61/275,092 filed Aug. 25, 2009, entitled "Accommodative Intraocular Lens", and is hereby incorporated into this application by reference as if fully set forth herein.

This patent application is related to patent application Ser. No. 11/549,818, Publication No. US 2007/0129803 A1, published Jun. 7, 2007, entitled "Accommodative Intraocular Lens," the entire contents of which is hereby incorporated herein by reference.

BACKGROUND OF THE INVENTION

1. Field of the Invention

The present invention is used in the field of medicine, and more particularly, can be used in ophthalmology as an intraocular lens for replacement of a cataract impaired natural lens.

2. Description of the Prior Art

The natural lens of the eye is often impaired by cataracts, particularly in older patients. Cataracts cloud the lens, increasing the opacity of the lens and thereby blurring or reducing the quality and clarity of the image provided to the retina by the lens. In extreme cases, the ability to distinguish an image is lost. A remedy which restores vision is available. Removal of the cataract impaired lens and replacement with an implantable artificial lens is an increasingly typical medical procedure for middle aged and elderly patients. A number of materials may be used in forming the artificial replacement lens, commonly known as an intraocular lens. Among these materials are acrylics, silicones, and hydrogels. All of these materials have a refractive index suitable for use as a intraocular lens. Most typically, these implantable intraocular replacement lenses are monofocal lens. Recently, bifocal intraocular lenses have been developed which include a small central region with a fixed second power focus adapted for near vision conditions.

One significant challenge is that an intraocular lens is located in an environment subject to muscular movement or adjustment as the patient changes the focus of viewing between distance viewing and near viewing. In the natural lens, ciliary muscles and fibrils tense in near vision situations to incrementally alter the lens shape slightly and thereby alter the focal length of the natural lens and increase the lens power, moving it forward and thickening or steepening the optical quality to facilitate sharper focus of near objects on the retina. This process is called accommodation. However, it should also be recognized that with aging, there occurs some loss of ability to exert accommodative muscle forces over the entire range of movement of a younger adult. Providing an intraocular lens which mimics the natural accommodation process associated with the ciliary muscles of the eye is an important goal for ophthalmology. One approach has been to supplement the implantable intraocular lens with a mechanical accommodation device which drives a small central portion axially in response to ciliary muscle tensing. Such mechanically driven devices, however, seem extraordinarily complex. For example, Brady et al., Pub. No. US2007/0100444, discloses a mechanically driven accommodating intraocular lens.

An alternative approach, disclosed in U.S. Pat. No. 6,638,305 by Laguette, following Portney U.S. Pat. No. 5,225,858, the entire disclosures of which are both incorporated herein by reference, is to employ an implantable intraocular lens with a relatively rigid outer portion and a relatively highly deformable inner core completely surrounded by the relatively rigid outer portion. The optical properties of the combination lens are altered by peripheral compressive squeezing to reshape the anterior face of the combination lens, thereby changing a first configuration of the combination lens with a single optical power into a second configuration of the combination lens with a plurality of optical powers.

It would be extremely desirable to provide an accommodating intraocular lens for replacement of cataract impaired natural lens, where such an accommodative lens was incrementally responsive to accommodative muscle tension in a manner more elegantly simple and in a manner which is more similar to that of the original unimpaired natural lens. The present invention advances the approach disclosed by Laguette in at least three ways, (1) by providing optical reshaping of both anterior and posterior surfaces by employing a core (i.e., inner lens portion) with a central location and deformable and resilient properties, (2) by accentuating the optical changes resulting from optical reshaping associated with deformation of the core by exposing the core on both anterior and posterior surfaces of the lens where the exposed anterior and posterior surfaces of the core are both optical surfaces of either spherical or aspherical optical shape, and (3) by providing an interface between the outer lens portion and the inner lens portion (i.e., core) which more efficiently drives the deformational reshaping of the core so as to allow aging patients to achieve accommodation in spite of some loss of accommodation force or range.

SUMMARY OF THE INVENTION

The general purpose of the present invention is to provide an accommodative intraocular lens capable of simulating a shift of artificial replacement optical lens properties of an intraocular lens in response to ciliary muscles and fibrils of the eye so as to facilitate viewing near objects.

Further, and more practically, procedures and teachings of the present invention can provide an accommodative intraocular lens which will response appropriately to attempts to focus vision on a near object such that viewing of the near object is facilitated and the image thereof sharpened by the accommodation or response of the intraocular lens of the present invention.

By "spherical" optic herein is meant an optic which has a surface with a constant radius of curvature. By "aspherical" optic herein is meant an optic which has a surface with a progressive or non-constant radius of curvature.

An accommodative intraocular lens of the present invention has an anterior side and a posterior side. The lens includes an outer lens portion and an inner lens portion. The outer lens portion has an anterior outer optic surface, a posterior outer optic surface, a peripheral edge located outwardly on the outer lens portion and an outer lens portion wall concentrically disposed with respected to the peripheral edge. The outer lens portion wall is centrally located in the outer lens portion and might be viewed as defining an aperture through the outer lens portion. The outer lens portion wall is directed inwardly and toward the inner lens portion. The inner lens portion has a diameter of from about 1.0 to 4.0 mm, more preferably about 1.5 to 2.5 mm, and most preferably about 2.0 mm. The inner lens portion has an exposed anterior inner optic surface, an exposed posterior inner optic surface, and an inner lens portion wall. The inner lens portion wall is directed outwardly toward the outer lens portion and, preferably, bonded or joined to the outer lens portion wall. These two walls are complementary in shape, such that if the inner lens portion wall is cylindrical, then the outer lens portion wall is also cylindrical and of similar diameter to that of the inner lens portion wall. If, alternatively, the inner lens portion wall is hourglass in shape, then the outer lens portion wall will have a complementary hourglass shape and be in intimate contact with the inner lens portion wall. In other words, the inner lens portion or core might be viewed as filling the aperture defined in the outer lens portion by the outer lens portion wall. The inner lens portion is formed of a soft deformable resilient material, softer than the outer lens portion material. The inner lens portion is alternatively termed a core. Compression at the peripheral edge of the outer lens portion, compresses the inner lens portion, such that the exposed anterior inner optic surface and the exposed posterior inner optic surface each steepen in shape. Additionally, the exposed anterior inner optic surface and the exposed posterior inner optic surfaces are driven apart from each other by compression of the core or inner lens portion. This bulging or steepening of both the anterior and posterior inner lens optic shapes alters the optical properties of the inner lens portion. Preferably, the compression at the peripheral edge of the outer lens portion is from about 0 to about 9.0 grams, more preferably from about 1.0 grams to about 5.0 grams, and most preferably about 5 grams. The movement associated with such compressive motion results in a decrease in diameter of the capsular bag of about roughly 1 mm. This is the compression force supplied by the ciliary muscle structure and zonules in accommodation associated with attempts to focus vision on near objects. Preferably, the inner lens portion wall has a generally cylindrical shape, with an exposed anterior inner optic surface on an anterior end of the generally cylindrical shape and an exposed posterior inner optic surface on a posterior end of the generally cylindrical shape. Compression of the peripheral edge of the outer lens portion reduces the diameter of the generally cylindrical shape and modifies the exposed anterior inner optic surface and the exposed posterior inner optic surface to steeper optic shapes. In a preferred embodiment, the inner lens portion and the outer lens portion both have spherical optic surfaces (prior to compression). In a first alternative embodiment, the outer lens portion has spherical optic surfaces and the inner lens portion has aspherical optic surfaces. In a second alternative embodiment, the outer lens portion has aspherical optic surfaces and the inner lens portion has spherical optic surfaces. In a third embodiment, the inner lens portion and the outer lens portion both have aspherical optic surfaces.

In yet another preferred embodiment, the present invention is an accommodative intraocular lens core, the core having a soft deformable resilient shape with an exposed anterior inner optic surface, an exposed posterior inner optic surface, and an inner lens portion wall extending therebetween. Compression of the core at the inner lens portion wall, between the exposed anterior inner optic surface and the exposed posterior inner optic surface, results in deformation of the exposed anterior inner optic surface and the exposed posterior inner optic surface. This deformation or bulging steepen the optic properties of each. The inner lens portion wall is preferably generally cylindrical. The generally cylindrical inner lens portion wall has a diameter, when compressed, smaller than the diameter when uncompressed. Preferably, the uncompressed diameter is from about 1.0 to about 4.0 mm. Alternatively, the accommodative intraocular lens core has an ellipsoid shape when compressed or has an hourglass shape.

In yet another embodiment, the present invention is a method of providing an accommodative intraocular lens. The method includes the steps of providing an outer lens portion, the outer lens portion having an anterior outer optic surface, a posterior outer optic surface, a peripheral edge, and an outer lens portion wall concentrically disposed with respect to the peripheral edge. Next, an inner lens portion is provided, the inner lens portion having an exposed anterior inner optic surface, an exposed posterior inner optic surface, and an inner lens portion wall which is disposed therebetween, the inner lens portion being formed of a soft deformable resilient material, softer than the outer lens portion material. The inner lens portion wall is bonded to the outer lens portion wall, with the anterior inner optic surface exposed and surrounded by the anterior outer optic surface, and with the posterior inner optic surface exposed and surrounded by the posterior outer optic surface, such that compression at the peripheral edge of the outer lens portion results in bulging of the anterior inner optic surface and the posterior inner optic surface.

In still another embodiment, the present invention is a method of providing accommodative near vision with an intraocular lens. The method includes the steps of providing an accommodative intraocular lens, with an outer lens portion and an inner lens portion bonded into the outer lens portion. The outer lens portion, having an anterior outer optic surface and a posterior outer optic surface, the outer lens having a peripheral edge and an outer lens portion wall concentrically disposed with respect to the peripheral edge. The inner lens portion has an exposed anterior inner optic surface, an exposed posterior inner optic surface, and an inner lens portion wall which is disposed therebetween, with the inner lens portion wall bonded to the outer lens portion wall, the inner lens portion is formed of a soft deformable resilient material, softer than the outer lens portion material. Compression at the peripheral edge of the outer lens portion, compresses the inner lens portion, such that the exposed anterior inner optic surface and the exposed posterior inner optic surface each steepen in shape. This intraocular lens is implanted in the capsule with the anterior outer optic surface and the exposed anterior inner optic surface directed anteriorly and the peripheral edge in contact with the capsule. When attempting to focus on a near object, compression bears against the peripheral edge and the anterior inner optic surface bulges anteriorly and the posterior inner optic surface bulges posteriorly. This enables a near focus by accommodation which is a very close approximation of the natural action of the eye.

In still another embodiment, the present invention is an accommodative intraocular lens including an outer lens and a core which serves as a changeable inner lens portion. The outer lens portion has a peripheral edge, an outer lens portion wall defining an aperture axially positioned in the outer lens portion, an anterior outer lens optic surface, and a posterior outer lens optic surface. The core is softer than the outer lens portion and is compressively situated in the aperture defined by the outer lens portion wall of the outer lens portion. The core defines or serves as an inner lens portion with an exposed anterior inner optic surface and an exposed posterior inner optic surface. When accommodative force applied to the peripheral edge of the outer lens portion that accommodative force further compresses the core to alter the anterior inner optic surface and the posterior inner optic surface such that near vision is improved. Optionally, the outer lens portion may further include a plurality of struts radially distributed therein and extending from adjacent the peripheral edge of the outer lens portion to the outer lens portion wall of the outer lens portion. The anterior outer lens optic surface is preferably an aspherical lens shape. The posterior outer lens optic surface is also preferably an aspherical lens shape. The anterior inner lens optic surface is preferably a spherical lens shape. The posterior inner lens optic surface is preferably a spherical lens shape. Preferably, the anterior inner lens optic surface is an aspherical lens shape after accommodative force compresses the core. Preferably, the posterior inner lens optic surface is an aspherical lens shape after accommodative force compresses the core. Preferably, the core has an inner lens portion wall, prior to compressive situation within the aperture, which is selected from the group of shapes consisting of: cylindrical, hourglass or bulging. Preferably, the core has an inner lens portion wall, subsequent to compressive situation within the aperture, which is selected from the group of shapes consisting of: cylindrical, hourglass or bulging. Preferably, the core has an inner lens portion wall, when subject to accommodative force when compressively situated within the aperture, which is selected from the group of shapes consisting of: cylindrical, hourglass or bulging.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

It should also be clearly understood and cautioned that the accompanying drawings are highly schematic in nature in order to better facilitate comprehension and promote understanding of the present invention. Thus, the depictions in the accompanying drawings exaggerate and distort certain features and details illustrated therein for teaching purposes. For these reasons, the accompanying drawings should not be employed for purposes, such as, for example, measuring angles and distances and proportions, which are inconsistent with their schematic character.

DETAILED DESCRIPTION OF THE PREFERRED EMBODIMENTS

Figure 1:
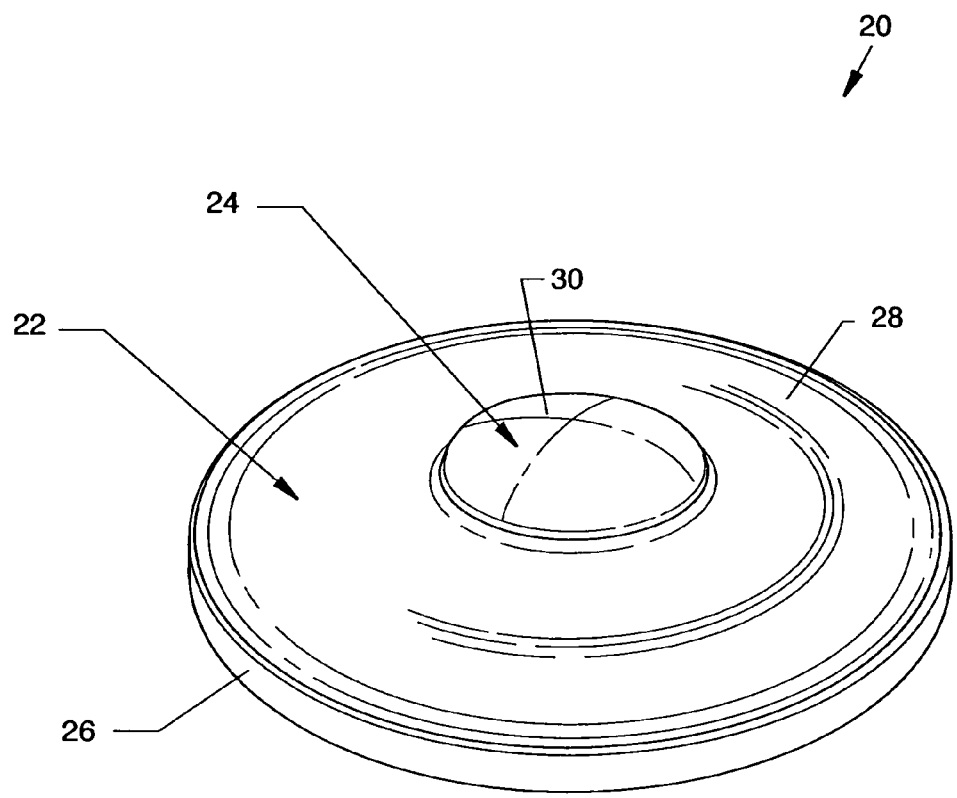
FIG. 1 is an isometric view of an accommodative intraocular lens, the present invention.

FIG. 1 is an isometric view of an accommodative intraocular lens 20, the present invention. The accommodative intraocular lens 20 has an outer lens portion 22 and an inner lens portion 24. The outer lens portion 22 has a peripheral edge 26 and an anterior outer optic surface 28. The inner lens portion 24 is centrally situated within the outer lens portion 22 and has an anterior inner optic surface 30 which is exposed, anteriorly, on the anterior side of the accommodative intraocular lens 20. In the accommodative intraocular lens 20, the outer lens 22 is characterized by having a spherical optic shape in the shape of the anterior outer optic surface 28. Other surfaces and features are referenced in FIG. 2, as well as in other illustrations.

Figure 2:
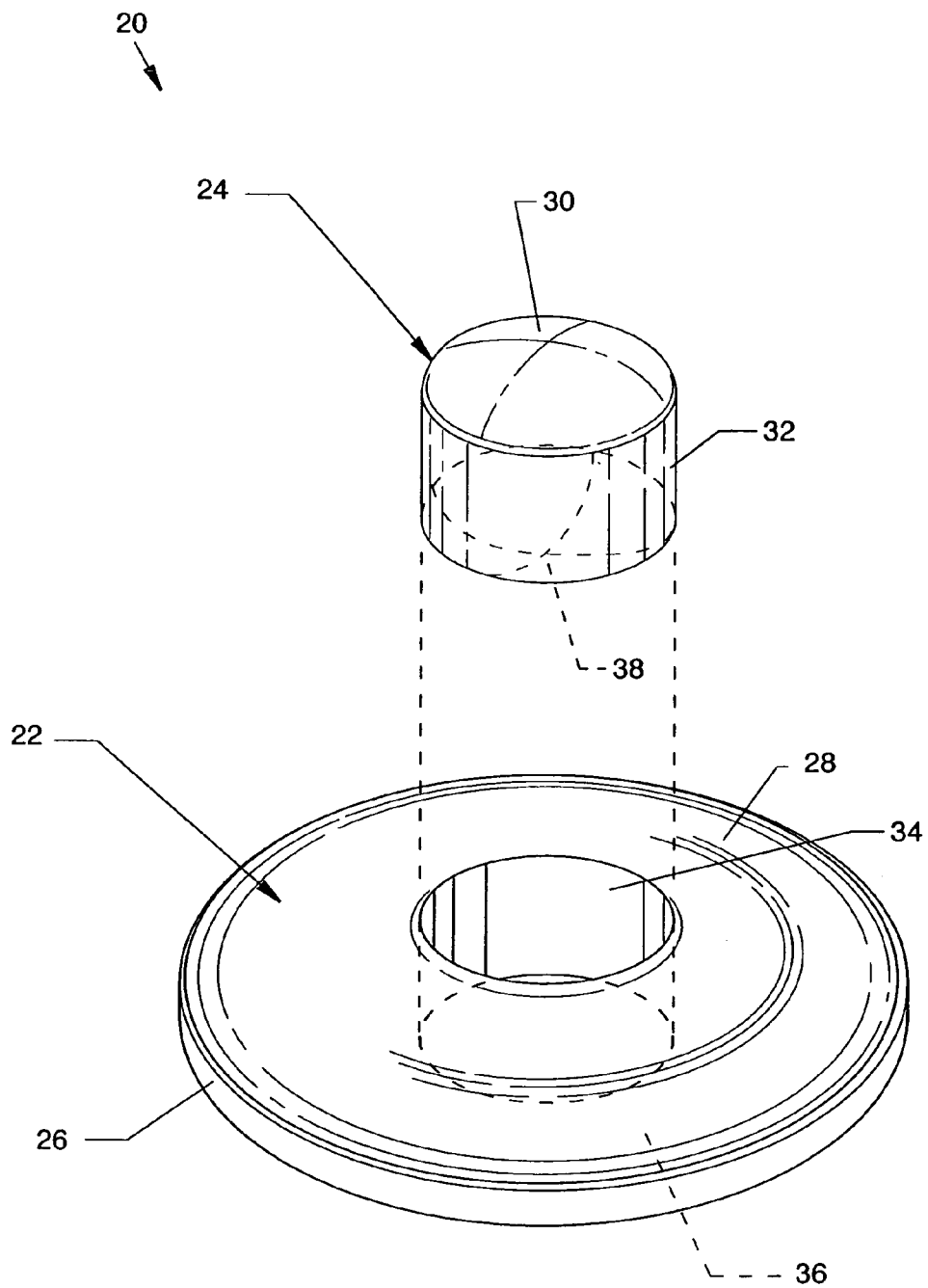
FIG. 2 is an exploded isometric view of the accommodative intraocular lens of FIG. 1 showing the inner lens portion separated from the outer lens portion.

FIG. 2 is an exploded isometric view of the accommodative intraocular lens 20 of FIG. 1 with the inner lens portion 24 shown exploded or separated from the outer lens portion 22. While the inner lens portion wall 32 is depicted in this view as separated from the outer lens portion wall 34, normally in this embodiment the inner lens portion wall 32 is bonded or joined to the outer lens portion wall 34 and is complementary therewith. The inner lens portion 24 is softer and more easily deformed than the outer lens portion 22. When implanted in the eye, inward movement of outer lens portion wall 34 (radially inward from compression applied at the peripheral edge 26) associated with accommodative ciliary muscle movement and zonule fibers or zonules, discussed subsequently, acts upon inner lens portion wall 32 to deform the inner lens portion 24, thereby simultaneously altering and steepening or bulging the anterior inner optic surface 30. Additionally, and related to such resilient deformation, the anterior inner optic surface 30 is driven anteriorly and axially away from the anterior outer optic surface 28, most especially at the center or axis 40 region of the anterior inner optic surface 30. Alternatively, when peripheral compression is reduced, the outer lens portion wall 34 resiliently moves outwardly (relatively outwardly toward the peripheral edge 26), the inner lens wall portion 32 also moves outwardly. Under such a situation, the inner lens portion 24, resiliently undeforms and relieves the steepening or bulging, thereby unaltering and slightly flattening the exposed spherical anterior inner optic surface 30 and also moving the anterior inner optic surface 30 toward the central mass of the inner lens portion 24. Similar action occurs at the exposed spherical posterior inner optic surface 38, which also simultaneously bulges and steepens in optical properties in response to compression of the inner lens portion wall 32. As with anterior inner optic surface 30, posterior inner optic surface 38 also resiliently returns to precompression shape and optical properties when compression on inner lens portion wall 32 is relieved.

In other words, the inner lens portion 24 might be comprehended as a centralized soft core easily deformed by compression and resilient in character. When the inner lens portion wall 32 of the relatively soft core is compressed, anterior inner optic surface 30 bulges outward (axially and anteriorly) and alters the shape of the anterior inner optic surface 30, modifying and steepening the optical properties thereof. When compression on the core is released, the original core shape is regained or restored, and the bulging at the anterior inner optic surface 30 is thus simultaneously relieved and returns to precompression shape and optical properties. Posterior inner optic surface 38 functions similarly, bulging in a posterior direction and steepening its optical properties. Note further that both anterior inner optic surface 30 and posterior inner optic surface 38 not only steepen in optical properties, but also the separation distance therebetween increases. Note moreover that light passing through both optical surfaces 30 and 38 will be acted upon by both optical surfaces so that a small change in each will result in a larger cumulative change at the retina, thereby facilitating near vision in a nearly natural accommodation by an accommodative intraocular lens 20.

It should also be pointed out that while the inner lens portion 24 of the accommodative intraocular lens 20 of this invention is depicted and explained as having a cylindrical body within inner lens portion wall 32, and also that while such a cylindrical body is a preferred embodiment, other shapes, preferably radially symmetrical shapes, are believed to provide similar actions to that of a cylindrical inner lens portion wall 32. For example, an hourglass shaped soft deformable resilient core shape with exposed optical surfaces or ends might further accentuate the steepening or bulging modification of the exposed optical surfaces or ends or alternatively reduce the compression force required to elicit the desirable steepening or bulging of the optical surfaces or ends, but an hourglass shape would also likely represent a more challenging manufacturing task than a cylindrically shaped core with exposed optical surfaces or ends and/or represent a durability challenge in maintaining the bond between complementary walls 32 and 34. It should also be pointed out that outer lens portion 22 and the inner lens portion 24 are both resilient and resume original, undeformed shapes when deformation forces are reduced or eliminated. Also, for example, a sphere shaped soft deformable resilient core with exposed optical ends might be compressed to a ellipsoid or "rugby ball" shape with optic surfaces or ends of the ellipsoid or "rugby ball" oriented axially, exposed anteriorly and posteriorly, but would also likely represent a manufacturing challenge.

Materials for the outer lens portion 22 and the inner lens portion 24 are any biocompatible material with an appropriate refractive index, i.e., of from about 1.40 to about 1.60. The inner lens portion 24 preferably has a diameter based upon the preferred inner lens portion wall 32 of about 1.0 to about 4.0 mm in diameter, more preferably about 1.5 to about 2.0 mm in diameter, and most preferably about 1.8 mm in diameter. Non-cylindrical embodiments have roughly similar sizes.

Figure 3A:
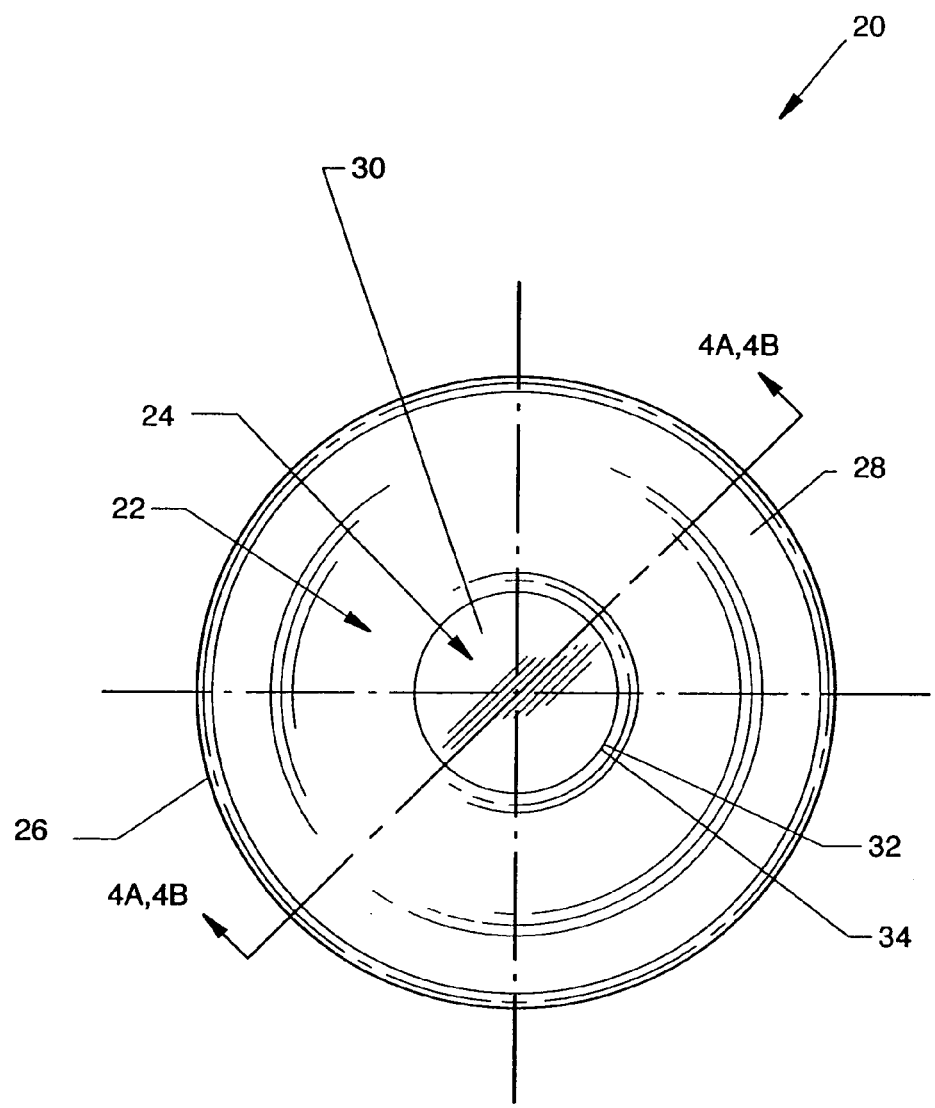
FIGS. 3A and 3B are anterior and posterior views, respectively, of the accommodative intraocular lens of FIG. 1.
Figure 3B:
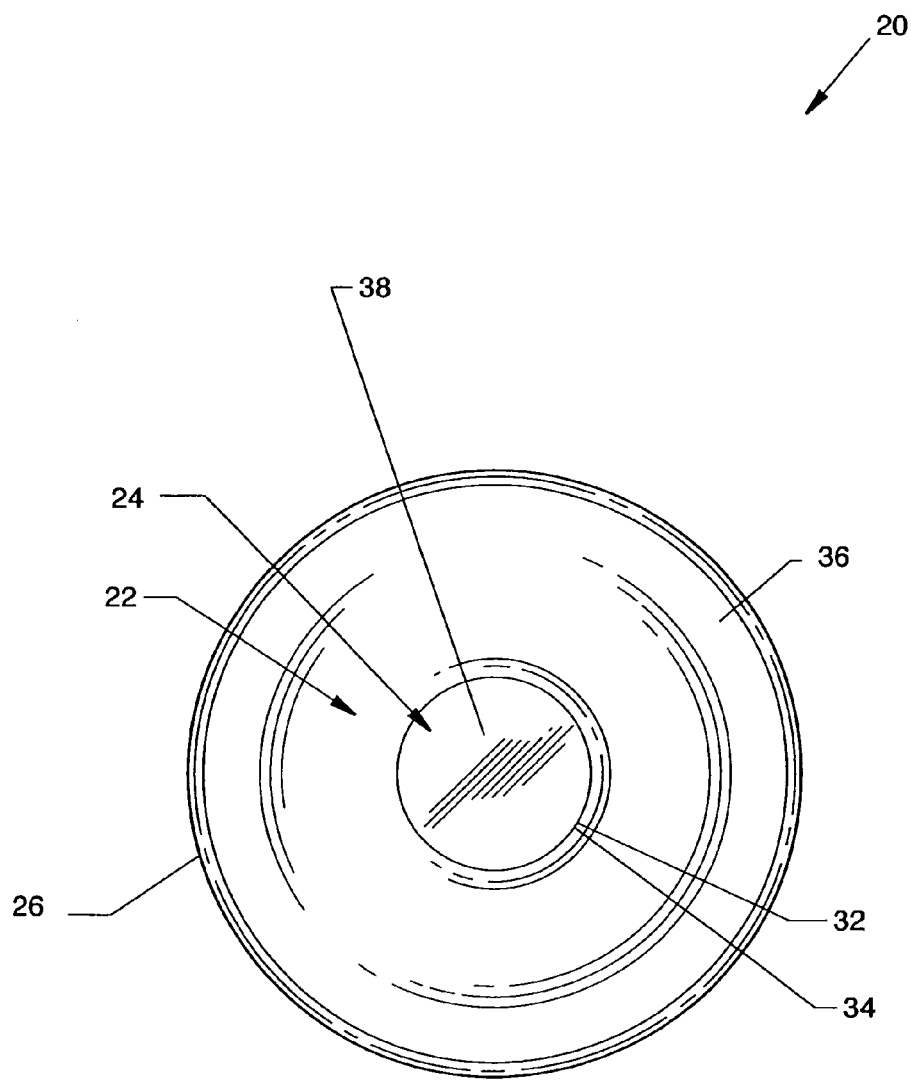

FIG. 3A is an anterior view of the accommodative intraocular lens 20 of FIG. 1, and FIG. 3B is a posterior view of the accommodating intraocular lens 20 of FIG. 1. Posterior outer optic surface 36, spherical, and posterior inner optic surface 38, spherical, are both visible in FIG. 3B. Inward movement of outer lens portion wall 34, associated with accommodative muscle tensing, discussed subsequently, acts upon inner lens portion wall 32 to deform the inner lens portion 24, thereby also altering and steepening or bulging the posterior inner optic surface 38. Additionally, and related to such deformation, the posterior inner optic surface 38 is driven axially away from the posterior outer optic surface 36, most preferentially at or near or adjacent to the center or axial region of the anterior inner optic surface 38.

Figure 4A:
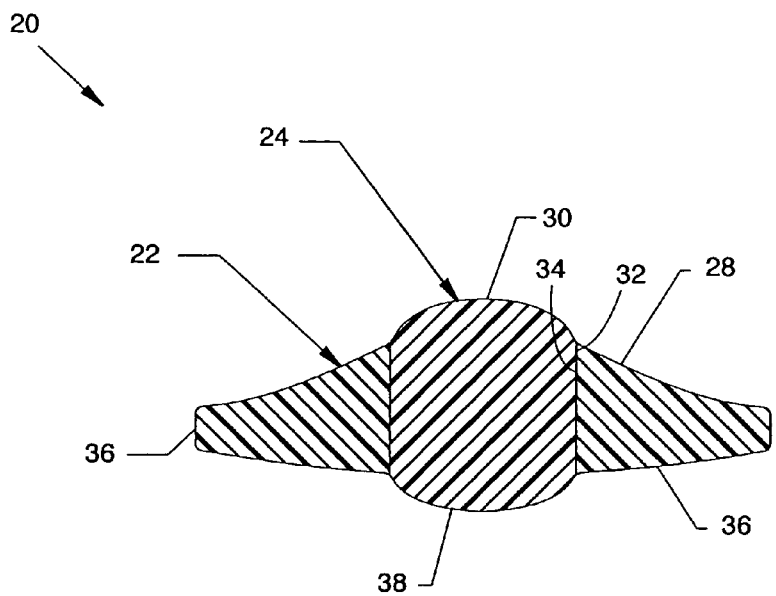
FIG. 4A is a cross section view at line 4A-4A of FIG. 3A showing the accommodative intraocular lens of FIG. 1 in a relaxed state.
Figure 4B:
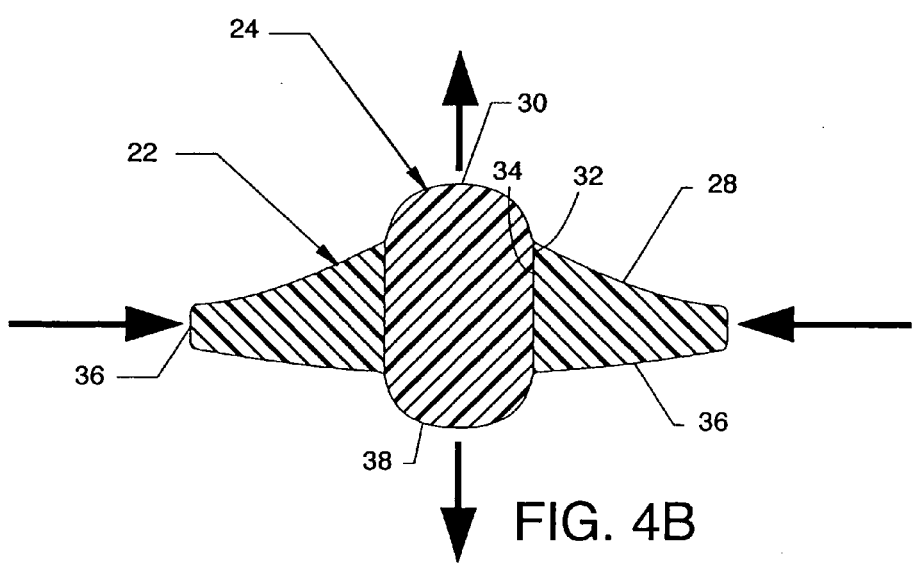
FIG. 4B is a cross section view at line 4B-4B of FIG. 3A showing the accommodative intraocular lens of FIG. 1 in a compressed state.

FIG. 4A depicts a cross section view of the accommodative intraocular lens 20 of FIG. 1 along line 4A-4A of FIG. 3A, shown in a relaxed condition present when a distant object is being viewed and low muscle tension is present. FIG. 4B is a cross section view of the accommodating intraocular lens 20 of FIG. 1 along line 4B-4B of FIG. 3A, shown in a compressed condition present when a near object is being viewed and ciliary muscle structure is tensed. Note that when compressed, due to muscle tensing, the shapes of both anterior inner optic surface 30 and posterior inner optic surface 38 are steepened and tend to move axially away from anterior outer optic surface 28 and posterior outer optic surface 36, respectively, due to deformation of the relatively softer and more easily deformed inner lens portion 24. This movement is most apparent adjacent to or at the axis 40 of the accommodative intraocular lens 20.

Figure 5A:
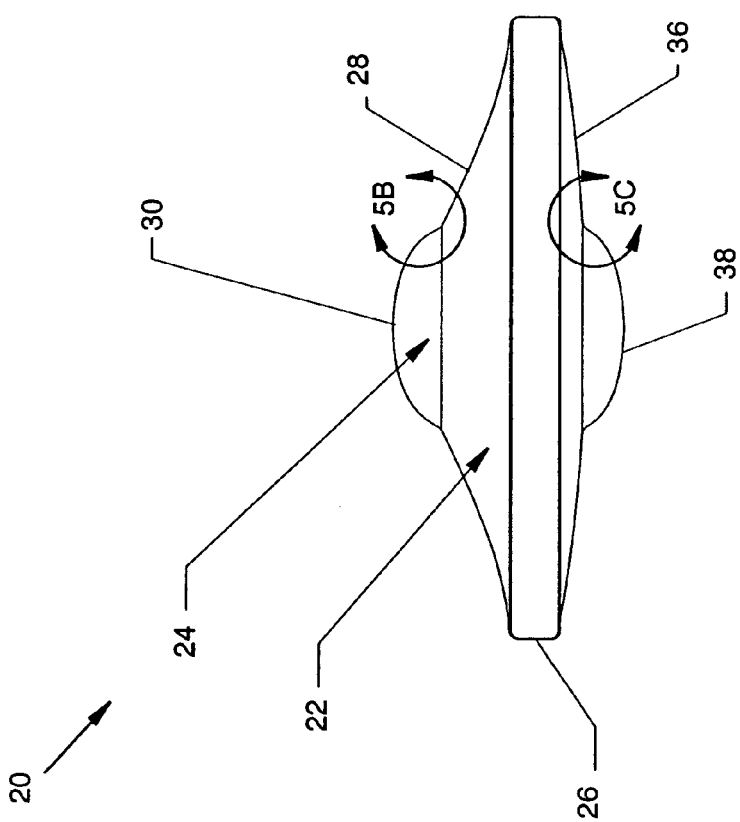
FIG. 5A is a side view of the accommodative intraocular lens of FIG. 1.
Figure 5B:
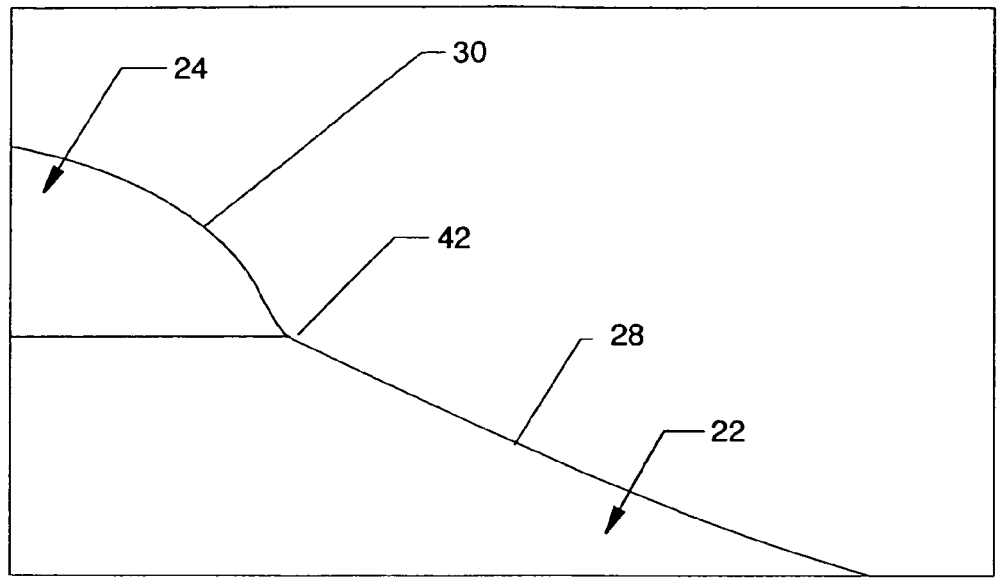
FIGS. 5B and 5C are detailed views of portions of FIG. 5A showing the transition between inner lens portion and outer lens portion on the anterior and posterior, respectively, of the accommodative intraocular lens of FIG. 1.
Figure 5C:
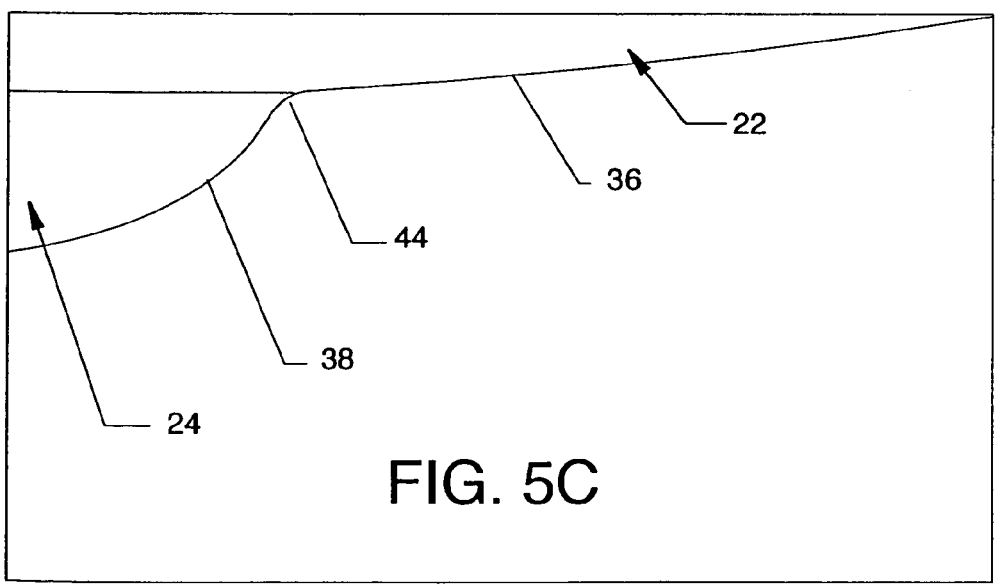

FIG. 5A is a side view of accommodative intraocular lens 20 of FIG. 1. FIG. 5B is a detailed side view of the transition at portion 5B of FIG. 5A. FIG. 5C is a detailed side view at portion 5C of FIG. 5A. While the transition is depicted in exaggerated form, the present invention is optionally and preferably subjected to polishing to remove any flash remaining from manufacture and to ease the transition present between anterior inner optic surface 30 and anterior outer optic surface 28, as well at the transition present between posterior inner optic surface 38 and posterior outer optic surface 36. The resulting anterior smoothed transition 42 and posterior smoothed transition 44 are depicted in detailed side view of FIGS. 5B and 5C, respectively. Smoothing of transitions has been previously disclosed in J. Stuart Cumming, et al., Pub. No. US2007/0129803 filed Jun. 7, 2007, incorporated in its entirety herein by reference.

Figure 6A:
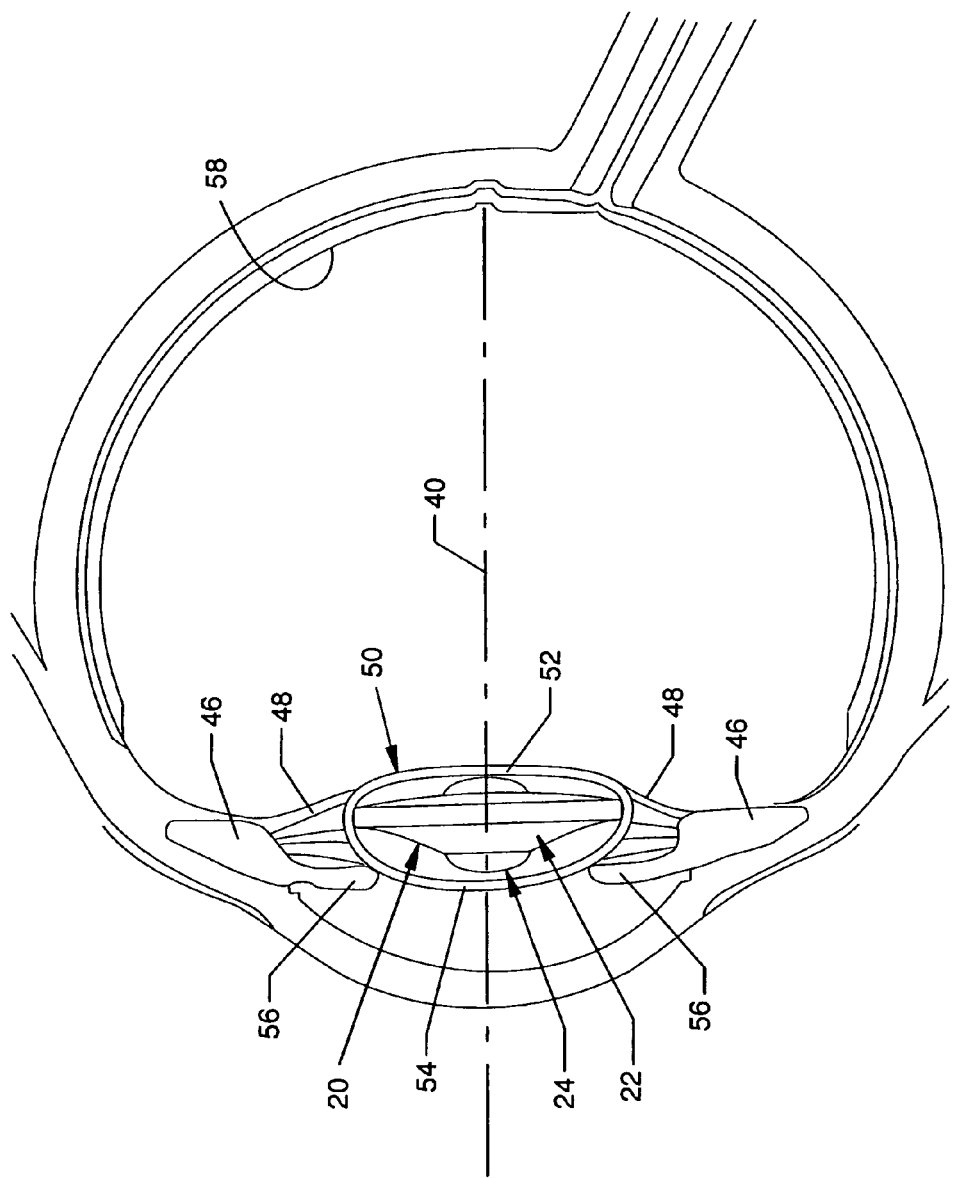
FIG. 6A depicts the accommodative intraocular lens of the present invention implanted in the capsule an eye.
Figure 6B:
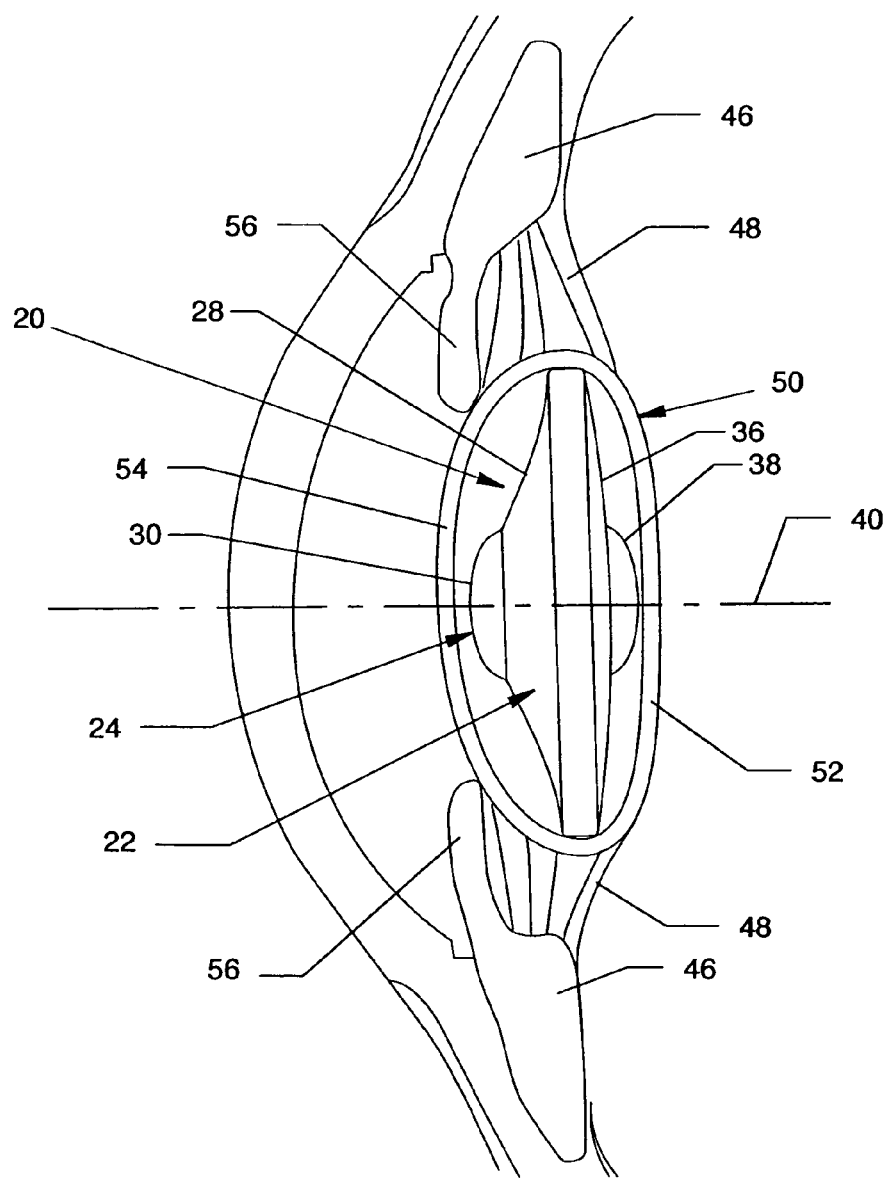
FIG. 6B depicts, in greater detail, the accommodative intraocular lens of the present invention in a relaxed state.
Figure 6C:
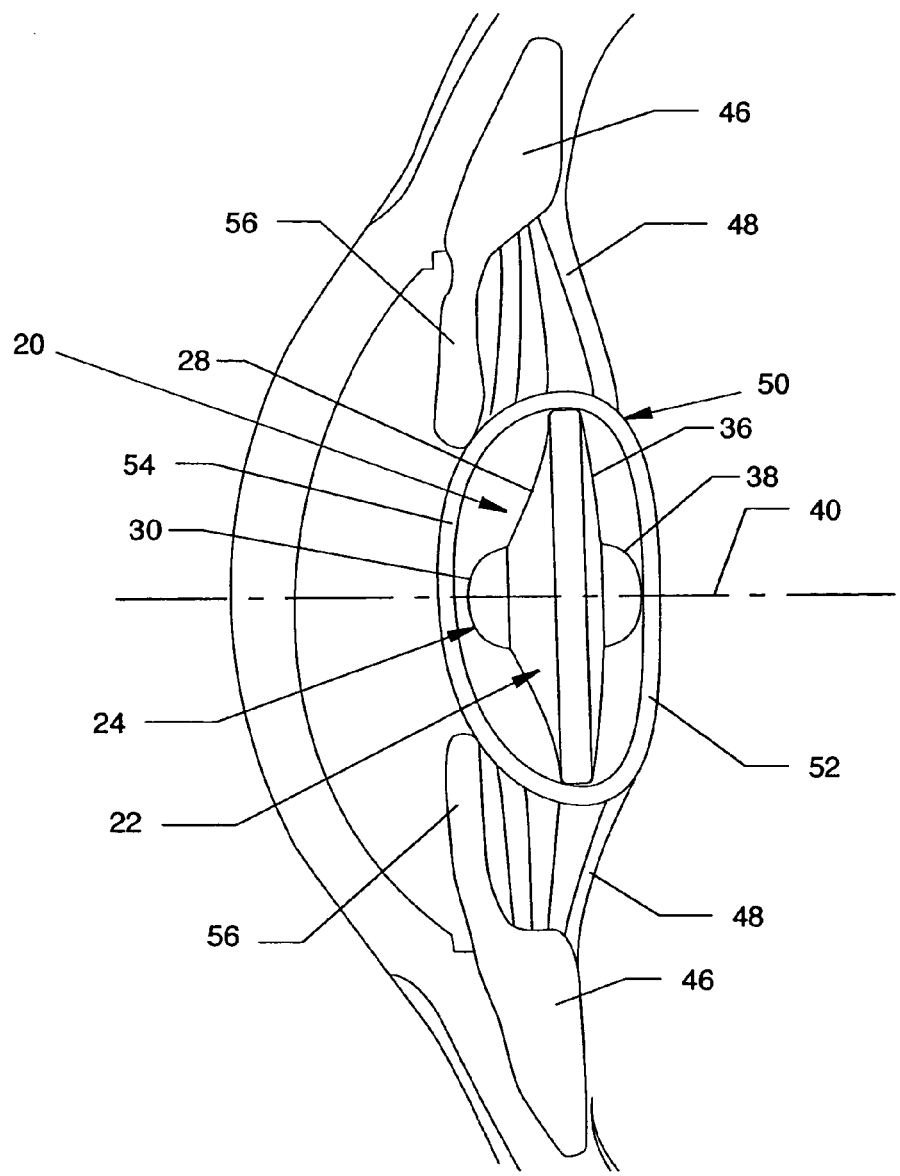
FIG. 6C depicts, in greater detail, the accommodative intraocular lens in a compressed state.

FIG. 6A is a schematic depiction of the eye 45 with the accommodative intraocular lens 20 of the present invention implanted therein and replacing the natural lens of the eye 45. While all portions of the eye 45 are not shown, orientation and understanding of the present invention will be advanced by noting the ciliary muscles 46, the fibers 48 leading to the capsule 50. The capsule 50 includes a posterior capsule wall 52 and an anterior capsule wall 54 centered behind iris 56 and the opening thereof. The axis 40 extends through the anteriorly and the posteriorly and eventually to the retina 58. The accommodative intraocular lens 20 of the present invention is implanted in the capsule 50, typically replacing a cataract impaired natural lens by surgical techniques well known in this art. FIG. 6B is a detailed schematic depiction of the accommodative intraocular lens 20 of the present invention implanted in the eye 45 interacting with ciliary muscles 46 through fibers 48 under relaxed conditions as the eye 45 views a distant object. FIG. 6C is a detailed schematic depiction of the accommodative intraocular lens 20 of the present invention implanted in the eye 45 and interacting with the tensed ciliary muscle 46 pulling fibers 48 as the eye views a near object. When capsule 50 is expanded away from axis 40, as in FIG. 6B, the inner lens portion 24 is not compressed. In this condition, the anterior inner optic surface 30 and the posterior inner optic surface 38 have a relatively flatter shape than when, as depicted in FIG. 6C, the capsule 50 is compressed by tightening in the ciliary muscles 46 pulling upon fibers 48. This, in turn, compresses the accommodative intraocular lens 20, deforming the inner lens portion 24, such that the anterior inner optic surface 30 and the posterior inner optic surface 38 steepen and move axially along axial 40 away from anterior outer optical surface 28 and posterior outer optical surface 36, respectively. The bulging (steepening and axial movement) increases the optic power afforded by the inner lens portion 24 facilitating near vision in an accommodative manner similar to that of a natural lens. By softening the nature of the inner lens portion 24 to allow sufficient deformation at lower force or reduced range, the accommodative intraocular lens 20 of the present invention can accommodate the aging eye and, at least, partially restore the near vision originally experienced before the onset of presbyopia.

Figure 7:
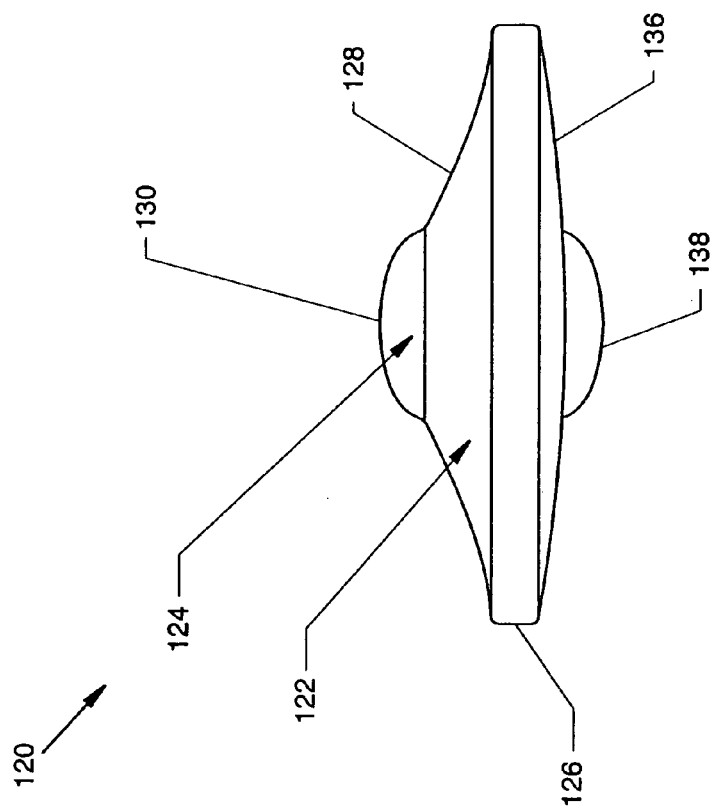
FIG. 7 depicts a side view of a first alternative embodiment of the present invention.

FIG. 7 depicts a first alternative embodiment, an accommodative intraocular lens 120 having a spherical outer lens portion 122, bounded by peripheral edge 126 and having spherical anterior and posterior outer optic surfaces 128 and 136, respectively, and an inner lens portion 124 with the anterior inner optic surface 130 and the posterior inner optic surface 138, each having aspherical optic shapes. As with the accommodative intraocular lens 20 of the first embodiment, the anterior inner optic surface 130 and the posterior inner optic surface 138 both deform and steepen in optical performance in response to tightening of ciliary muscle to cause an increase in power and facilitate near vision.

Figure 8:
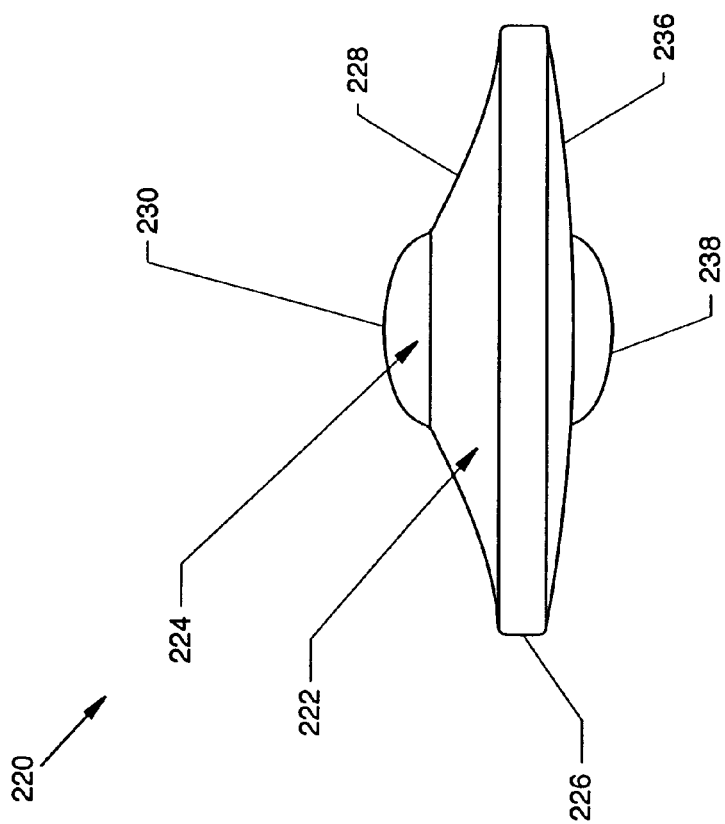
FIG. 8 depicts a side view of a second alternative embodiment of the present invention.

FIG. 8 depicts a second alternative embodiment, an accommodative intraocular lens 220 having an aspherical outer lens portion 222, bounded by peripheral edge 226 and having aspherical anterior and posterior outer optic surfaces 228 and 236, respectively, and a spherical inner lens portion 224 with spherical lens shapes on both the anterior inner optic surface 230 and the posterior inner optic surface 238. As with the accommodative intraocular lens 20 of the first embodiment, the anterior inner optic surface 230 and the posterior inner optic surface 238 both deform and steepen in optical performance in response to tightening of ciliary muscle to cause an increase in power and facilitate near vision.

Figure 9:
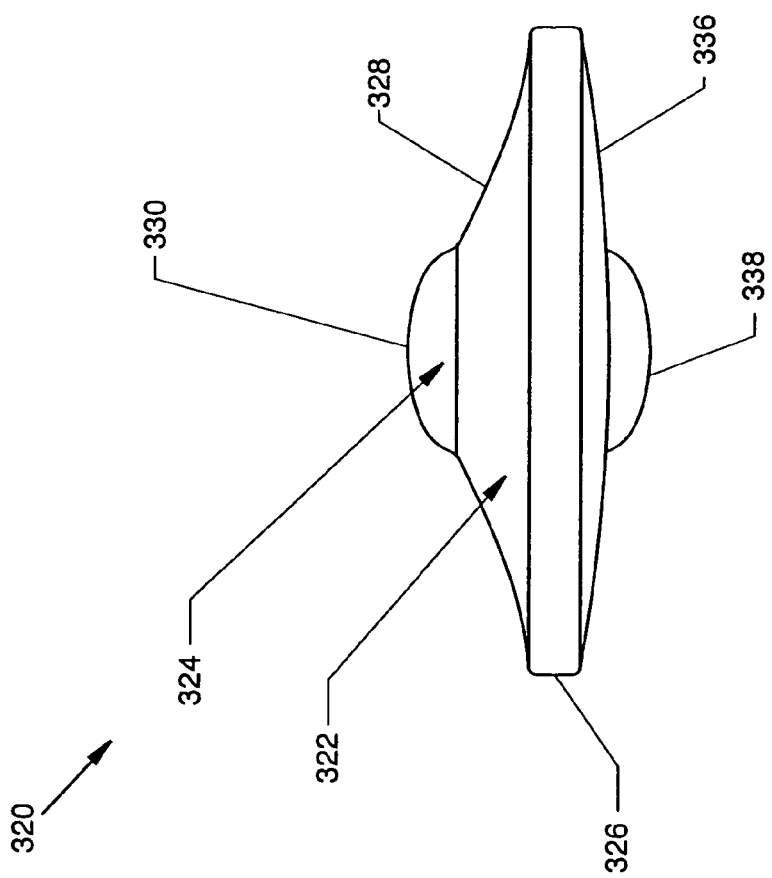
FIG. 9 depicts a side view of a third alternative embodiment of the present invention.

FIG. 9 depicts a third alternative embodiment, an accommodative intraocular lens 320 having an aspherical outer lens portion 322, bounded by peripheral edge 326 and having aspherical anterior and posterior outer optic surfaces 328 and 336, respectively, and an inner lens portion 324 with aspherical lens shapes on the anterior inner optic surface 330 and the posterior inner optic surface 338. As with the accommodative intraocular lens 20 of the first embodiment, the anterior inner optic surface 330 and the posterior inner optic surface 338 both deform and steepen in optical performance in response to tightening of ciliary muscle to cause an increase in power and facilitate near vision.

MODE OF OPERATION

The accommodative intraocular lens 20 of the present invention functions by deforming the inner lens portion 24 to steepen both the anterior inner optic surface 30 and the posterior inner optic surface 38 exposed anteriorly and posteriorly, respectively, within the capsule 50 in response to ciliary muscle 46 tensing, thereby altering the near vision available in an incremental manner. Note that the anterior inner optic surface 30 and the posterior inner optic surface 38 also move away from each other, allowing the associated optic power of the inner lens portion 24 to be further altered and preferably increased during accommodation of ciliary muscle 46 tensing. Also, the pupil of the eye is typically reduced in diameter slightly during accommodation, thus the inner lens portion 24 will represent a greater fraction of the intraocular lens 20 acting on a light image, thereby increasing the effectiveness of the accommodative intraocular lens of the present invention. However, in low light situations, such as night driving, the pupil tends to maximum diameter and de-emphasizes the inner lens portion 24 and utilizes the image formed primarily by the outer lens portion 22 of the accommodative intraocular lens 20 of the present invention.

Given the explanation, details, critical relationships and understanding of this disclosure, it is within the skill of the art to provide a suitable flexible and resilient material for the outer lens portion 22 and a suitable soft center material which is deformable and resilient and bonded in a central position for the inner lens portion 24. It is also within the skill in the art, given the explanation, details, critical relationships and understanding of this disclosure, to provide sizing and dimensions and proportions in both the outer lens portion 22 and the inner lens portion 24 and all optic surfaces associated therewith.

Figure 10A:
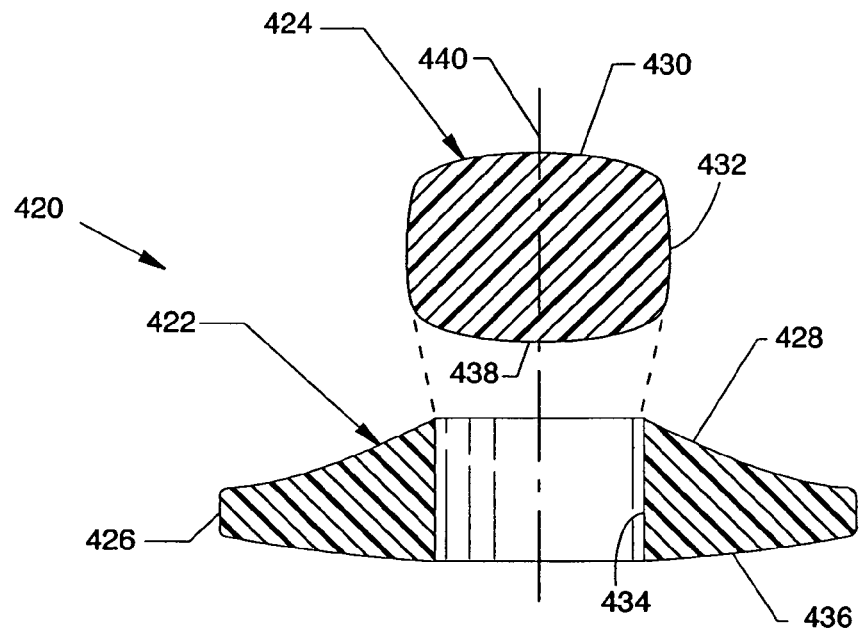
FIGS. 10A, 10B and 10C depict cross section views of a fourth alternative embodiment of the present invention in pre-assembled, assembled/relaxed, and accommodation/compressed conditions, respectfully.

FIG. 10A depicts a cross section view of components of a fourth alternative embodiment 420 of the present invention accommodative intraocular lens prior to assembly. In particular, fourth embodiment accommodative intraocular lens 420 includes an outer lens portion 422 and an inner lens portion or core 424. The outer lens portion 422 has a peripheral edge 426 and an anterior outer optic surface 428. The outer lens portion 422 also has an outer lens portion wall 434 defining an aperture in the outer lens portion 422. The inner lens portion or core 424 has an inner lens portion wall 432, an anterior inner optic surface 430, and a posterior inner optic surface 438. The outer lens portion 422 is resilient and flexible and the inner lens portion or core 424 is also resilient and flexible, but softer than the outer lens portion 422. A significant distinction of this fourth embodiment 420 is that the inner lens portion or core 424 has an inner lens portion wall 432 which is larger than the aperture defined by outer lens portion wall 434 and, therefore, is slightly compressed when situated within the aperture defined by outer portion wall 434, as subsequently depicted in FIG. 10B. Assembly, therefore, might involve cooling to contract the volume of the inner lens portion or core 424, or mechanical compression of inner lens portion wall 432 prior to insertion into the aperture defined by outer wall portion 434 or other like techniques, which result in the relatively softer inner lens portion or core 424 be slightly deformed to fit into the relatively firmer outer lens portion 422.

Figure 10B:
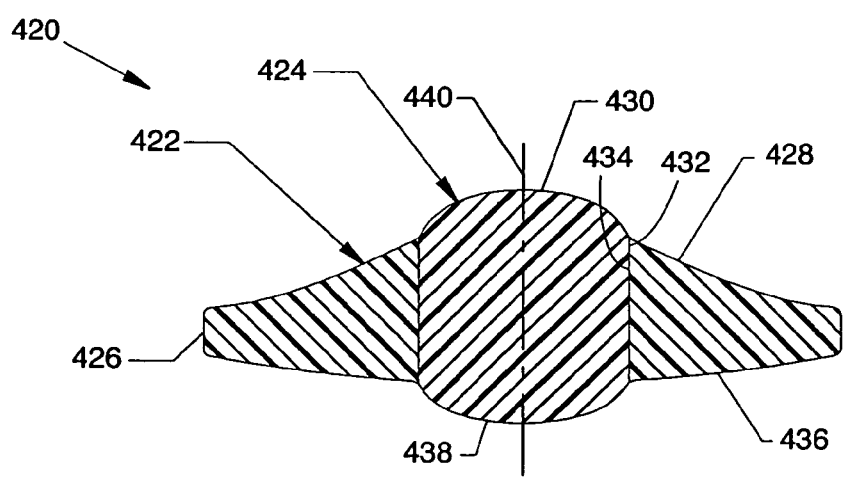

FIG. 10B depicts a cross section view of the fourth alternative embodiment 420 of the present invention in an assembled but generally relaxed condition, such as that experienced when distance vision is occurring. Note that the anterior inner optic surface 430 and the posterior inner optic surface 438 are slightly more steeply curved in such assembled but generally relaxed condition relative to the slightly less steeply curved anterior inner optic surface 430 and the posterior inner optic surface 438 of the unassembled inner lens portion or core 424 described prior to assembly. Also, note that the anterior inner optic surface 430 and the posterior inner optic surface 438 are slightly more axially displaced away from each other. In such assembled but generally relaxed condition, the fourth embodiment accommodative intraocular lens 420 is better prepared to reflect radially inwardly directed accommodative forces applied at the peripheral edge 426 as deformation changes to the prestressed inner lens portion or core 424 which, in turn, usefully modify the shapes of anterior inner optic surface 430 and the posterior inner optic surface 438 to facilitate near vision, when compared to embodiments lacking the prestressed relationship between the relatively softer inner lens portion or core 424 and the outer lens portion 422.

Figure 10C:
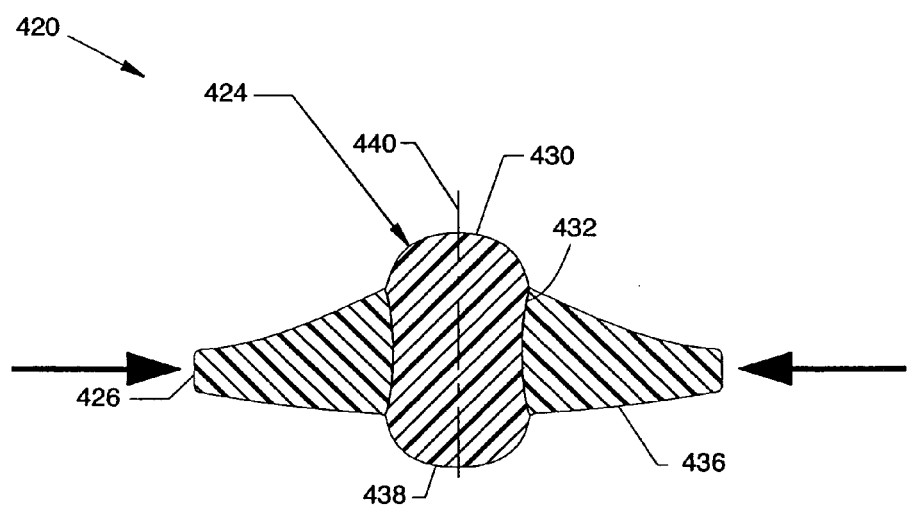

FIG. 10C depicts a cross section view of the fourth alternative embodiment 420 of the present invention in accommodation/compressed condition as experienced in near vision. Note that the anterior inner optic surface 430 and the posterior inner optic surface 438 are depicted as steeper and further separated from each other, thereby allowing more power for facilitating near vision. Note, also, that the deformation of outer lens portion wall 434 and inner lens portion wall 432 has not been depicted as retaining a cylindrical shape but rather as an hourglass or radially inwardly bulgingly deformed relationship.

Figure 11A:
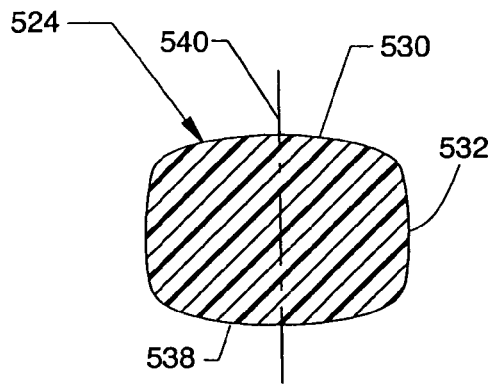
FIGS. 11A, 11B and 11C depict cross section views of three alternatively shaped embodiments of a core (i.e., an inner lens portion) of the present invention; and, FIGS. 12A, 12B and 12C depict an exploded perspective view, a cross section view at 12B-12B of FIG. 12C and an anterior view, respectively, of yet another embodiment of the present invention, including struts in the outer lens portion.

FIG. 11A depicts a cross section view of an alternatively shaped embodiment of a core 524 (i.e., an inner lens portion) of the present invention. In the depicted embodiment 524, the inner wall portion 532 bulges radially outwardly, with the greatest extent of the bulge situated roughly about half way between the anterior inner optic surface 530 and the posterior inner optic surface 538. If such a core 524 is inserted into a generally cylindrically shaped aperture, then the greatest prestressed deformation of such a core 524 would be expected to also be situated roughly about half way between the anterior inner optic surface 530 and the posterior inner optic surface 538.

Figure 11B:
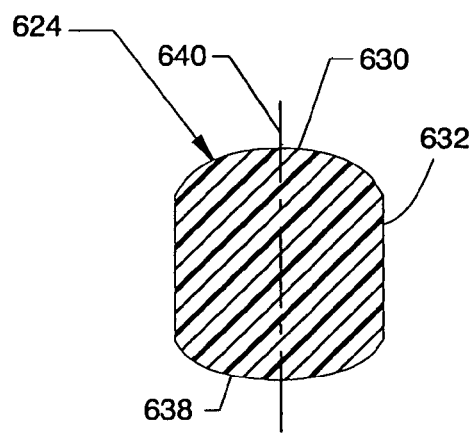

FIG. 11B depicts a cross section view of a second alternatively shaped embodiment of a core 624 (i.e., an inner lens portion) of the present invention. In the depicted embodiment 624, the inner wall portion 632 is generally cylindrically shaped. If such a core 624 is inserted into a generally cylindrically shaped aperture, then the prestressed deformation of such a core 624 would be expected to also be generally uniformly distributed between the anterior inner optic surface 630 and the posterior inner optic surface 638.

Figure 11C:
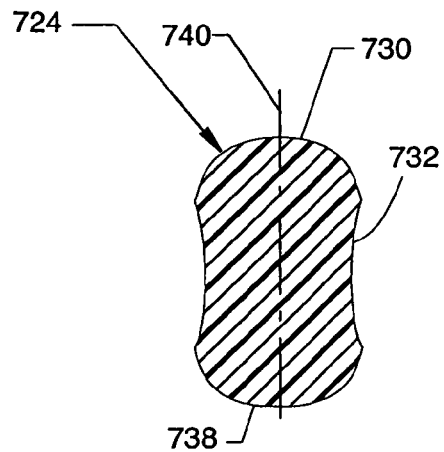

FIG. 11C depicts a cross section views of a third alternatively shaped embodiment of a core 724 (i.e., an inner lens portion) of the present invention. In the depicted embodiment 724, the inner wall portion 732 is somewhat hourglass in shape, bulging radially inwardly, with the greatest extent of the radial inward bulge situated roughly about half way between the anterior inner optic surface 730 and the posterior inner optic surface 738. If such a core 724 is inserted into a generally cylindrically shaped aperture, then the greatest prestressed deformation of such a core 724 would be expected to be situated roughly adjacent to the anterior inner optic surface 730 and the posterior inner optic surface 738. Thus, by a comparison of the features and expected performance of the three alternatively shaped, soft, deformable, resilient cores 524, 624 and 724, herein disclosed, deformation performance of a soft centrally situated inner portion of an accommodative intraocular lens may be selectably provided for an accommodative core having an anterior inner optic surface and a posterior inner optic surface, both of which surfaces increase in diopter power in response to accommodative forces. Additionally, it may be possible to selectively modify the shape of the aperture defined by the outer lens portion wall to advantageously apply further prestress to a selected core, for example, such as depicted for embodiments 524, 624, and 724.

Figure 12A:
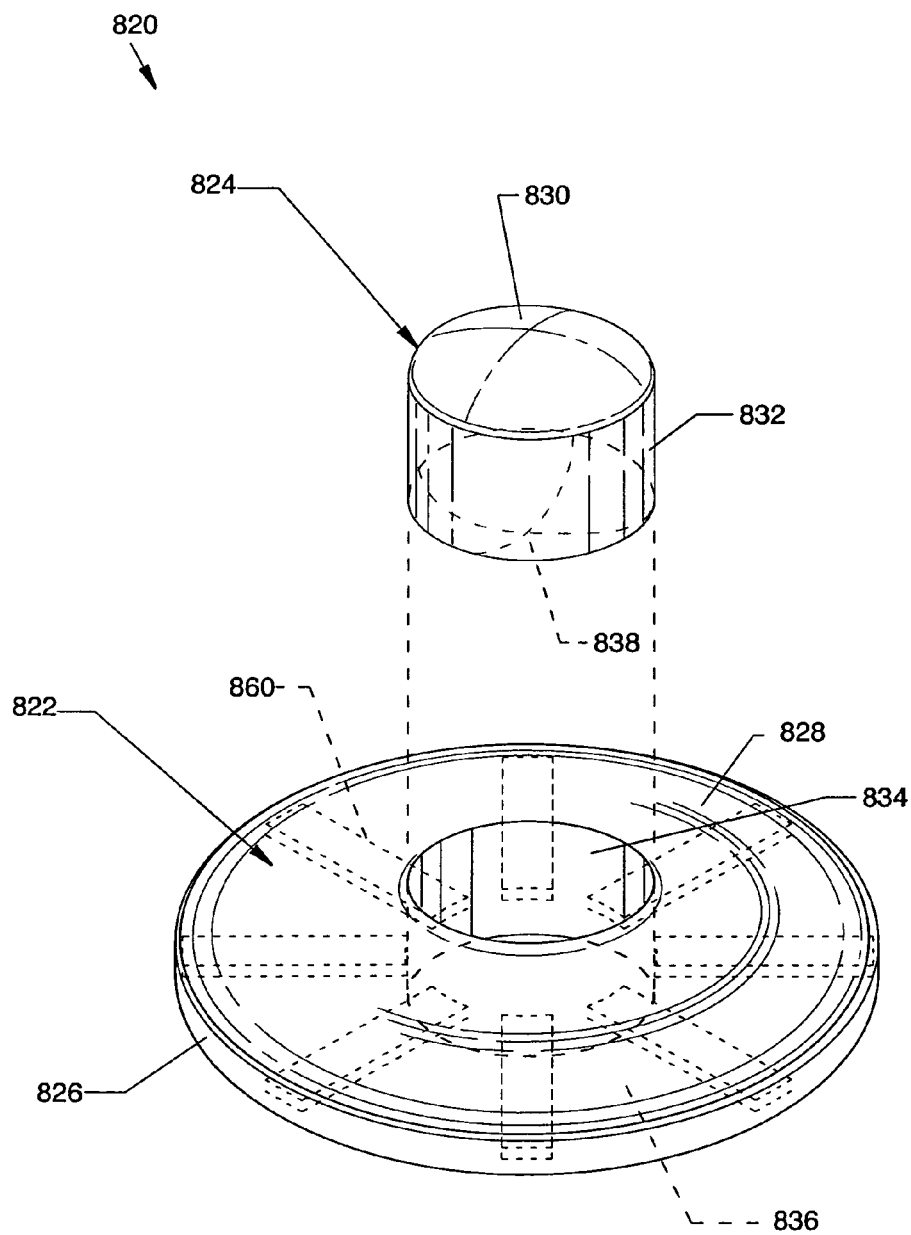

FIG. 12A depicts an exploded perspective view of yet another embodiment 820 of the present invention, including struts 860, depicted in dashed outline, in the outer lens portion 822. The outer lens portion 822 has a peripheral edge 826, an anterior outer optic surface 828, a posterior outer optic surface 836, and an outer lens portion wall 834 defining an aperture centrally disposed in the outer lens 822. Struts 860 are elongated and extend radially from adjacent the outer lens portion wall 834 to adjacent the peripheral edge 826. Preferably, eight struts 860 are present and radially distributed in the outer lens portion 822, although other quantities of struts 860 might be employed. The struts 860 are generally optically invisible or negligible within the outer lens portion 822, and are situated generally between the anterior outer optic surface 828 and the posterior outer optic surface 836. The struts 860 are of relatively stiffer material than the rest of the outer lens portion 822 and, therefore, promote transmission efficiency of radially inwardly directed accommodative forces from the peripheral edge 826 to the outer lens portion wall 834. Depicted in FIGS. 12A, B and C are struts 860 of generally rectangular cross section, however, other cross section shapes are also envisioned as substitutes for rectangular cross sections, such as round, oval, box, star. It is also envisioned that additional mechanisms might be employed and provided adjacent the peripheral edge 826 or the outer lens portion wall 834 to facilitate force transmission and/or prevent the depicted rectangular ends of the struts 860 from piercing the peripheral edge 826 or the outer lens portion wall 834. Such other mechanisms might include feet, etc., on either end of the struts 860. The compressive force applied to the outer lens portion wall 834, in turn, compresses the inner portion wall 832 of the softer inner portion or core 824, thereby resulting in reshaping of the anterior inner optic surface 830 and the posterior inner optic surface 838. Preferably, the core 824, is oversized relative to the aperture defined by the outer lens portion wall 834 such that it is subjected to compression without accommodative force applied to the peripheral edge 826. This precompression relationship is believed to more efficiently utilize the accommodative force, such that the more efficiently transmitted accommodative force resulting from the struts 860 is then more efficiently deforming the core 824 to cause maximum change in the anterior inner optic surface 830 and the posterior inner optic surface 838.

Figure 12B:
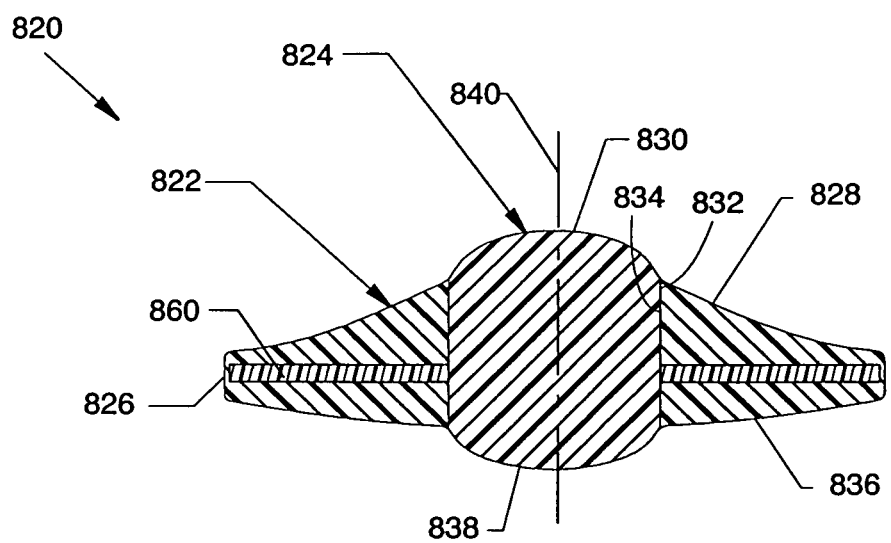
Figure 12C:
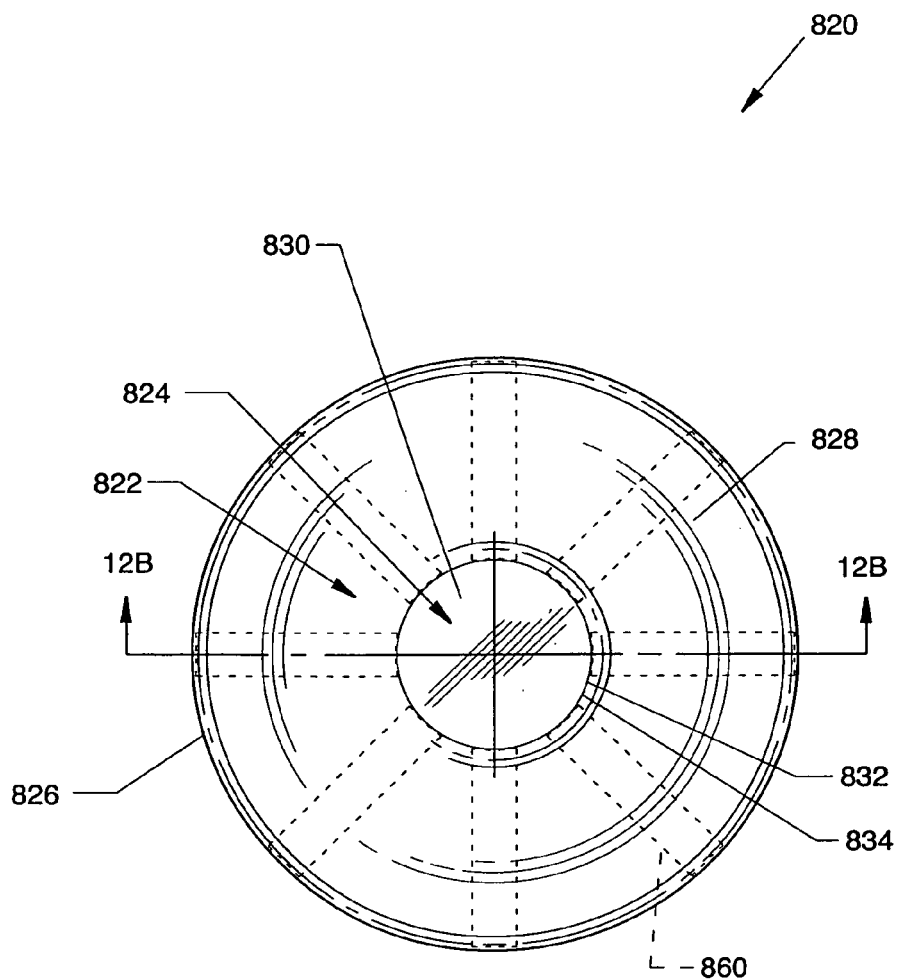

FIG. 12B depicts a cross section view at 12B-12B of FIG. 12C of the embodiment 820 of the present invention, including struts 860 depicted in dashed outline, in the outer lens portion 822, shown in FIG. 12A.

FIG. 12C depicts an anterior view of the embodiment 820 of the present invention, including struts 860 in the outer lens portion 820 depicted in dashed outline, shown in FIG. 12A.

Various modifications can be made to the present invention without departing from the apparent scope thereof.

ACCOMMODATIVE INTRAOCULAR LENS PARTS LIST 20 accommodative intraocular lens
22 outer lens portion
24 inner lens portion
26 peripheral edge
28 anterior outer optic surface
30 anterior inner optic surface
32 inner lens portion wall
34 outer lens portion wall
36 posterior outer optic surface
38 posterior inner optic surface
40 axis
42 anterior smoothed transition
44 posterior smoothed transition
45 eye
46 ciliary muscle
48 fibers
50 capsule
52 posterior capsule wall
54 anterior capsule wall
56 iris
58 retina 120 accommodative intraocular lens, a first alternative embodiment
122 spherical outer lens portion
124 inner lens portion
126 peripheral edge
128 spherical anterior outer optic surface
130 anterior inner optic surface
136 spherical posterior outer optic surface
138 posterior inner optic surface
220 accommodative intraocular lens, a second alternative embodiment
222 aspherical outer lens portion
224 spherical inner lens portion
226 peripheral edge
228 aspherical anterior outer optic surface
230 anterior inner optic surface
236 aspherical posterior outer optic surface
238 posterior inner optic surface
320 accommodative intraocular lens, a third alternative embodiment
322 aspherical outer lens portion
324 inner lens portion
326 peripheral edge
328 aspherical anterior outer optic surface
330 anterior inner optic surface
336 aspherical posterior outer optic surface
338 posterior inner optic surface
420 accommodative intraocular lens, a fourth alternative embodiment
422 outer lens portion
424 inner lens portion
426 peripheral edge
428 anterior outer optic surface
430 anterior inner optic surface
432 inner lens portion wall
434 outer lens portion wall
438 posterior inner optic surface
524 core (inner lens portion)
530 anterior inner optic surface
532 inner wall portion
538 posterior inner optic surface
624 core (inner lens portion)
630 anterior inner optic surface
632 inner wall portion
638 posterior inner optic surface
724 core (inner lens portion)
730 anterior inner optic surface
732 inner wall portion
738 posterior inner optic surface
820 accommodative intraocular lens
822 outer lens portion
824 inner portion or core
826 peripheral edge
828 anterior outer optic surface
830 anterior inner optic surface
832 inner portion wall
834 outer lens portion wall
836 posterior outer optic surface
838 posterior outer optic surface
860 struts

The invention claimed is:

1. An accommodative intraocular lens having an anterior side and a posterior side, comprising:
an outer lens portion having an anterior outer optic surface and a posterior outer optic surface, the outer lens portion having a continuous outer peripheral edge and a continuous inner annular wall portion disposed concentrically within said continuous outer peripheral edge so as to define a central hole within said outer lens portion such that said outer lens portion comprises a continuous annulus, said outer lens portion being fabricated from a predetermined material; and
an inner lens portion, separate and distinct from said outer lens portion, having an exposed anterior inner optic surface, an exposed posterior inner optic surface, and disposed within said central hole of said outer lens portion with an outer peripheral lens wall portion of said inner lens portion bonded to said inner annular wall portion of said outer lens portion, the inner lens portion being formed from a soft deformable resilient material which is softer than said predetermined material from which said outer lens portion is formed;
wherein radially inner compression forces disposed upon said outer peripheral edge of the outer lens portion will tend to radially inwardly compress the outer peripheral lens wall portion of said inner lens portion such that the exposed anterior inner optic surface and the exposed posterior optic surface will each be deformed axially outwardly away from each other.

2. The lens of claim 1, wherein the compression at the peripheral edge of the outer lens portion is from about 0 to about 9.0 grams.

3. The lens of claim 2, wherein the compression at the peripheral edge is from about 1.0 grams to about 5.0 grams.

4. The lens of claim 3, wherein the compression is about 5 grams.

5. The lens of claim 1, wherein the outer peripheral lens wall portion of said inner lens portion has a generally cylindrical shape, and wherein compression of the outer peripheral edge of the outer lens portion reduces the diameter of the generally cylindrical shape of said inner lens portion.

6. The accommodative intraocular lens of claim 1 wherein the anterior outer lens optic surface of said inner lens portion has an aspherical lens shape.

7. The accommodative intraocular lens of claim 1 wherein the posterior outer lens optic surface has an aspherical lens shape.

8. The accommodative intraocular lens of claim 1 wherein the anterior inner lens optic surface has an aspherical lens shape.

9. The accommodative intraocular lens of claim 8, wherein the anterior inner lens optic surface has an aspherical lens shape after accommodative forces compress the inner lens portion.

10. The accommodative intraocular lens of claim 1 wherein the posterior inner lens optic surface has a spherical lens shape.

11. The accommodative intraocular lens of claim 10, wherein the posterior inner lens optic surface has an aspherical lens shape after accommodative forces compress the inner lens portion.

12. The accommodative intraocular lens of claim 1 wherein the outer peripheral lens wall portion of said inner lens portion, prior to a radial compressive situation within the central hole of said outer lens portion, has a shape which is selected from the group of shapes consisting of: cylindrical, hourglass, and bulging.

13. The accommodative intraocular lens of claim 1 wherein the outer peripheral lens wall portion of said inner lens portion, subsequent to a radial compressive situation within the central hole of said outer lens portion, has a shape which is selected from the group of shapes consisting of: cylindrical, hourglass, and bulging.

14. The accommodative intraocular lens of claim 1 wherein the outer peripheral lens wall portion of said inner lens portion, when subject to accommodative forces when radially compressively situated within the central hole of said outer lens portion, has a shape which is selected from the group of shapes consisting of: cylindrical, hourglass, and bulging.

15. The lens of claim 1, wherein:
   said radially inner compression forces disposed upon said outer peripheral edge of the outer lens portion will also tend to deform the exposed anterior inner optic surface and the exposed posterior inner optic surface so as to effectively steepen the optics properties of said exposed anterior optic surface and said exposed posterior inner optic surface.

\* \* \* \* \*